(12) United States Patent
Albeck et al.

(10) Patent No.: US 10,251,703 B2
(45) Date of Patent: Apr. 9, 2019

(54) NERVE SPARING TREATMENT SYSTEMS AND METHODS

(71) Applicant: NERVESENSE LTD., Givat Shmuel (IL)

(72) Inventors: Dan David Albeck, Givat Shmuel (IL); Tzachi Itzhak Sabati, Megadim (IL)

(73) Assignee: NERVESENSE LTD., Givat Shmuel (IL)

( * ) Notice: Subject to any disclaimer, the term of this patent is extended or adjusted under 35 U.S.C. 154(b) by 0 days.

(21) Appl. No.: 15/607,688

(22) Filed: May 30, 2017

(65) Prior Publication Data

US 2017/0348052 A1 Dec. 7, 2017

Related U.S. Application Data

(63) Continuation of application No. 14/191,446, filed on Feb. 27, 2014, now abandoned.

(51) Int. Cl.
*A61N 5/06* (2006.01)
*A61B 18/14* (2006.01)
(Continued)

(52) U.S. Cl.
CPC ............ *A61B 18/22* (2013.01); *A61B 5/4836* (2013.01); *A61B 5/4893* (2013.01); *A61N 5/0622* (2013.01); *A61B 18/1492* (2013.01); *A61B 18/1815* (2013.01); *A61B 2017/00039* (2013.01); *A61B 2017/00119* (2013.01); *A61B 2017/00176* (2013.01); *A61B 2018/0066* (2013.01); *A61B 2018/00339* (2013.01); *A61B 2018/00547* (2013.01); *A61B 2018/00577* (2013.01); *A61B 2018/00642* (2013.01); *A61B 2018/00702* (2013.01);
(Continued)

(58) Field of Classification Search
None
See application file for complete search history.

(56) References Cited

U.S. PATENT DOCUMENTS 5,341,807 A * 8/1994 Nardella ............... A61B 5/0422
600/381
2004/0243112 A1* 12/2004 Bendett ............... A61F 9/00827
606/5
(Continued)

*Primary Examiner* — Carl H Layno
*Assistant Examiner* — Manolis Pahakis
(74) *Attorney, Agent, or Firm* — Pearl Cohen Zedek Latzer Baratz LLP

(57) ABSTRACT

Treatment systems are provided, which comprise a treatment element applying a treatment to a tissue, a stimulation element optically stimulating nerves in the tissue, a sensing unit sensing an electrical signal produced by nerves in the tissue in response to the optical stimulation, and a control unit controlling the application of the treatment according to the sensed signal. The systems and methods are used to avoid damaging nerves by sensing them during operation and immediately before local treatment application and preventing energy emission when the treatment tool is too close to specified nerves. Additional electric stimulation may be provided to enable avoidance of nerve damages on a larger scale, the treatment may be applied by a cold laser, and the control unit may control the treatment in realtime and in a closed loop and immediate prevent further treatment upon sensing optically stimulated nerves.

7 Claims, 16 Drawing Sheets

(51) Int. Cl.
*A61B 18/22* (2006.01)
*A61B 5/00* (2006.01)
*A61B 18/00* (2006.01)
*A61B 18/18* (2006.01)
*A61B 17/00* (2006.01)

(52) U.S. Cl.
CPC ............ *A61B 2018/00708* (2013.01); *A61B 2018/00732* (2013.01); *A61B 2018/00839* (2013.01); *A61B 2018/00898* (2013.01); *A61B 2018/00904* (2013.01)

(56) References Cited

U.S. PATENT DOCUMENTS

| | | | |
|---|---|---|---|
| 2008/0077198 A1* | 3/2008 | Webb | A61N 5/0618 607/88 |
| 2010/0049180 A1* | 2/2010 | Wells | A61N 5/0616 606/12 |
| 2010/0114190 A1* | 5/2010 | Bendett | A61N 1/36014 607/3 |
| 2014/0018792 A1* | 1/2014 | Gang | A61B 18/1492 606/41 |
| 2014/0276755 A1* | 9/2014 | Cao | A61N 5/00 606/33 |
| 2015/0238259 A1* | 8/2015 | Albeck | A61B 18/22 606/3 |

* cited by examiner

--Prior Art--

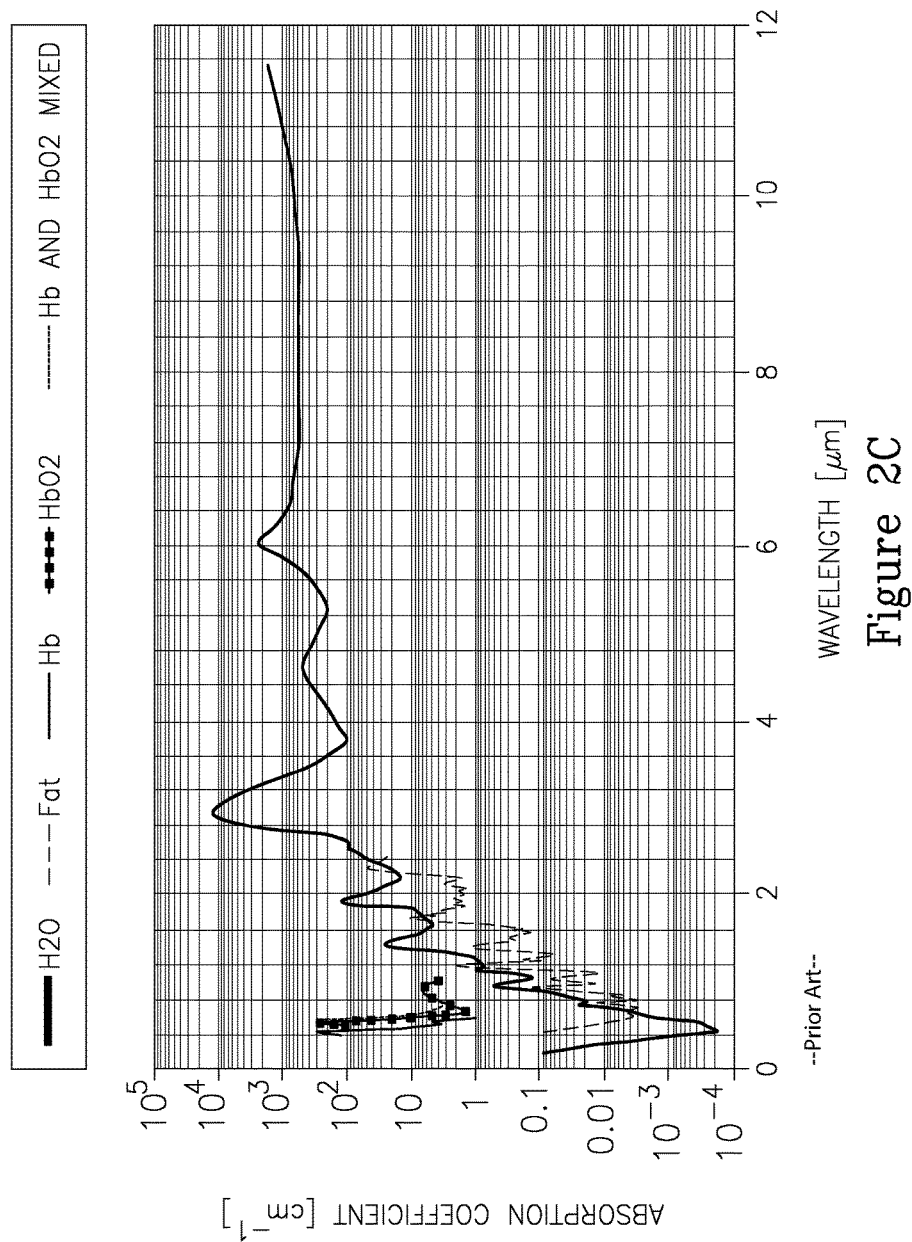

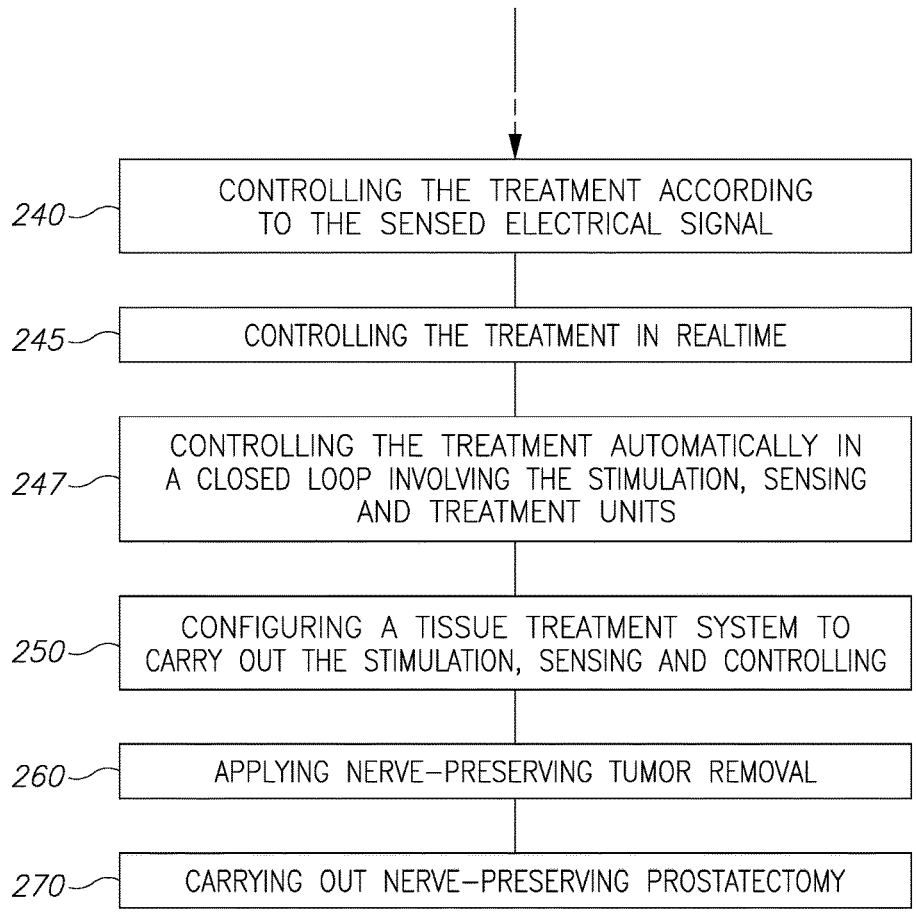
Figure 6 (cont. 1)

NERVE SPARING TREATMENT SYSTEMS AND METHODS

CROSS-REFERENCE TO RELATED APPLICATIONS

This application is a continuation of U.S. patent application Ser. No. 14/191,446, filed Feb. 27, 2014, which is hereby incorporated by reference.

BACKGROUND OF THE INVENTION

1. Technical Field

The present invention relates to the field of invasive surgery, and more particularly, to treatment tools which avoid damaging nerves.

2. Discussion of Related Art

It is common that nerves are damaged during surgical procedures, resulting in malfunctioning of associated sensory and motor systems. At least some of the damage is not a necessary result in view of the surgical targets and is in principle avoidable. Current technology includes mapping and/or monitoring of nerves by measuring nerve or organ response to electrical stimulation.

SUMMARY OF THE INVENTION

One aspect of the present invention provides a treatment system comprising a treatment unit comprising a treatment element arranged to apply a treatment to a tissue, a stimulation unit comprising a stimulation element arranged to stimulate nerves in the tissue, a sensing unit comprising a sensing electrode arranged to sense an electrical signal produced by nerves in the tissue in response to said stimulation, and a control unit arranged to control the application of the treatment according to the sensed electrical signal.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 2A-2D are illustrations of absorption and penetration of electromagnetic radiation with respect to water, fat and blood as proxies for the absorption and penetration of electromagnetic radiation into tissue.

DETAILED DESCRIPTION OF THE INVENTION

Figure 1A:
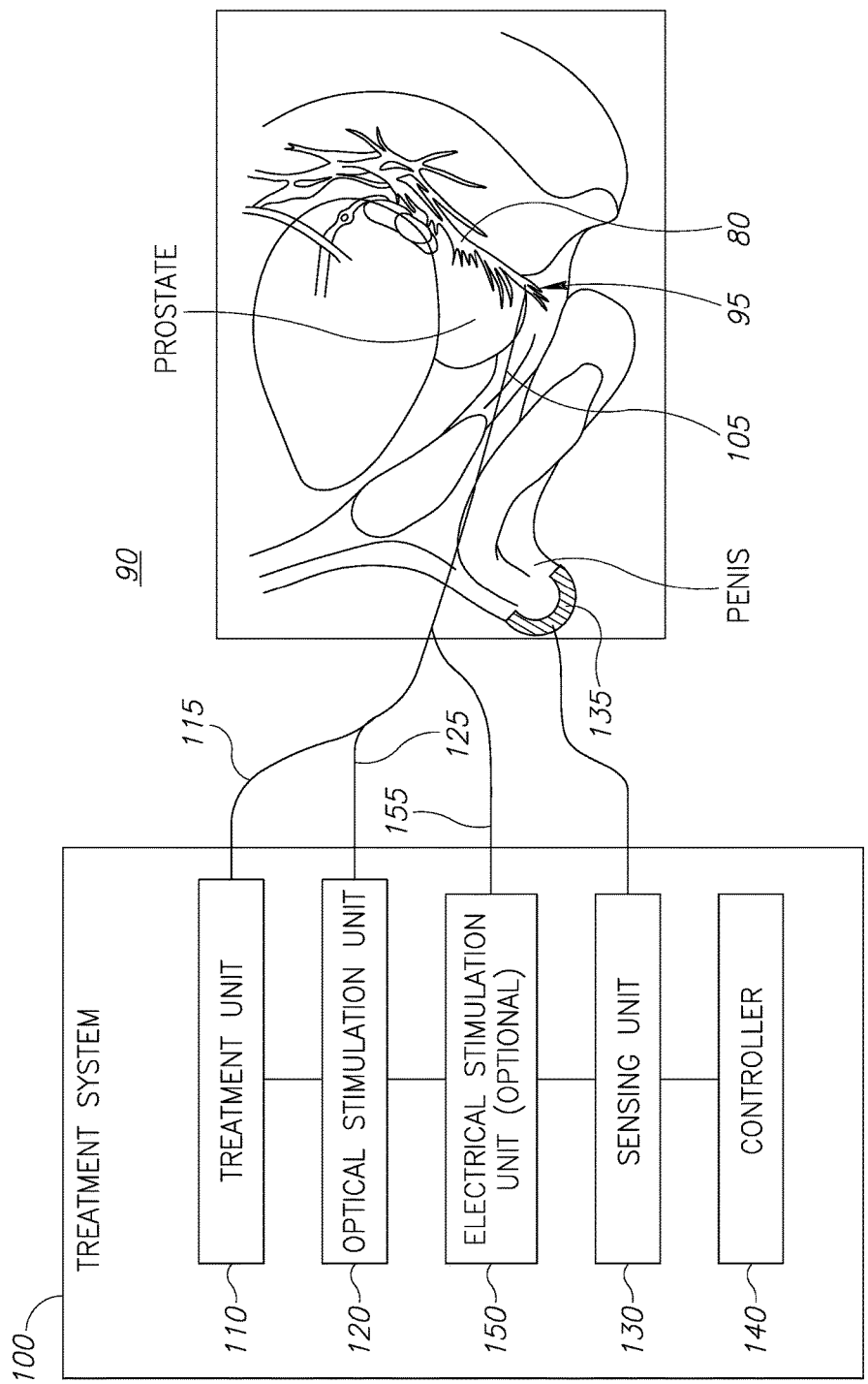
FIGS. 1A and 1B are high level schematic illustrations of treatment systems for treating the prostate and for microsurgery, respectively, according to some embodiments of the invention.

Prior to the detailed description being set forth, it may be helpful to set forth definitions of certain terms that will be used hereinafter.

The terms "light-based" and "optical" as used in this application refer to electromagnetic radiation in the visible range as well as in the near infrared range.

The term "cold laser" as used in this application refers to a laser that is configured to ablate tissue while preventing stress waves or heat from propagating beyond the interaction volume relative to a shortest dimension of the interaction volume. For example, a cold laser may deliver pulses or fast trains of pulses having energy per pulse or per train of pulses that is sufficient to heat an interaction volume of the tissue above the spinodal decomposition threshold for water within the pulse duration, and cause sufficient pressure for ejection of the target tissue. Such a cold laser may have the duration of the pulse or the train of pulses selected to be sufficiently short to prevent stress waves or heat from propagating beyond the interaction volume relative to a shortest dimension of the interaction volume. For example, such cold laser may comprise flash vaporization surgical systems such as those described in U.S. Patent Application Publication No. 2013/0035676, producing laser pulses having a wavelength between 1400 and 1520 nm or between 1860 and 2500 nm, having between 1 and 40 milli-joules per pulse, and having a pulse duration less than 200 nanoseconds.

The term "closed loop" as used in this application refers to a method of control which is automatic and does not involve manual activity.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The systems and methods which are described below optically stimulate nerves in a tissue volume which is about to be treated and are tuned to measure responses from the stimulated nerves immediately before the actual activation of the treatment, in real time. In case nerves are detected in the tissue volume, the treatment may be prevented, modified or attenuated in real time to avoid unnecessary damage to the nerves. In case of an optical treatment (such as a treatment using ablative laser), the optical stimulation may be advantageously be carried out in a configuration in which the stimulation radiation is arranged to penetrate the tissue into a larger volume than the optical treatment radiation. Such a configuration maintains safety margins to compensate for system, tissue, and procedure variations and for residual heat dissipation thermal damage. One option to ensure this safety margin is by using different wavelengths for the treatment and stimulation radiation in a way that the stimulation radiation penetrates the tissue into a larger volume than the treatment radiation. An additional electrical stimulation may further enhance nerve detection in and around the treated volume. Advantageously, the invention allows the surgeon to avoid iatrogenic damage to nerves. The systems and methods allow the surgeon to avoid mechanical damage (stretching, squashing, tearing, cutting, clamping, etc.) to nerves by identifying nerves in the treated region as well as to avoid thermal and electrical damages by using cold laser and/or attenuating or switching off the treatment energy when the treatment tool is too close to the nerves (used to prevent mechanical damage as well). Advantageously, combining non-contact optical treatment with optical stimulation and adjusting the treatment energy with respect to the proximity to the nerve allow the practitioner to treat tissue that is much closer to the nerves than is possible in conventional approaches without damaging the nerves. With respect to current surgical technologies and methods which do not sense nerves at all, or sense nerves only at a crude resolution and/or at specified time periods, the current invention advantageously enables high resolution localized measurements, enables realtime nerve sensing as well as a closed loop operation of the treatment tool which automatically avoids damaging nerves. For example, tools of the current invention may be used to remove tumors that are adjacent to nerves, scars on nerves, etc. by ablating the material to be removed up to the very circumference of the nerves, without damaging the nerves.

Specifically, in certain embodiments, electrical stimulation and respective sensing may be used as a long range sensing mechanism that allows avoiding mechanical damage to nerves, cold laser may be used as the treatment tool to avoid thermal and electrical damages to nerves, and optical stimulation and respective sensing may be used to prevent fine scale damage to nerves (accidental cutting), optionally automatically in a closed loop and in realtime. The latter aspect can be seen as turning the treatment tool into a "smart knife" that automatically avoids severing nerves in its way.

Figure 1B:
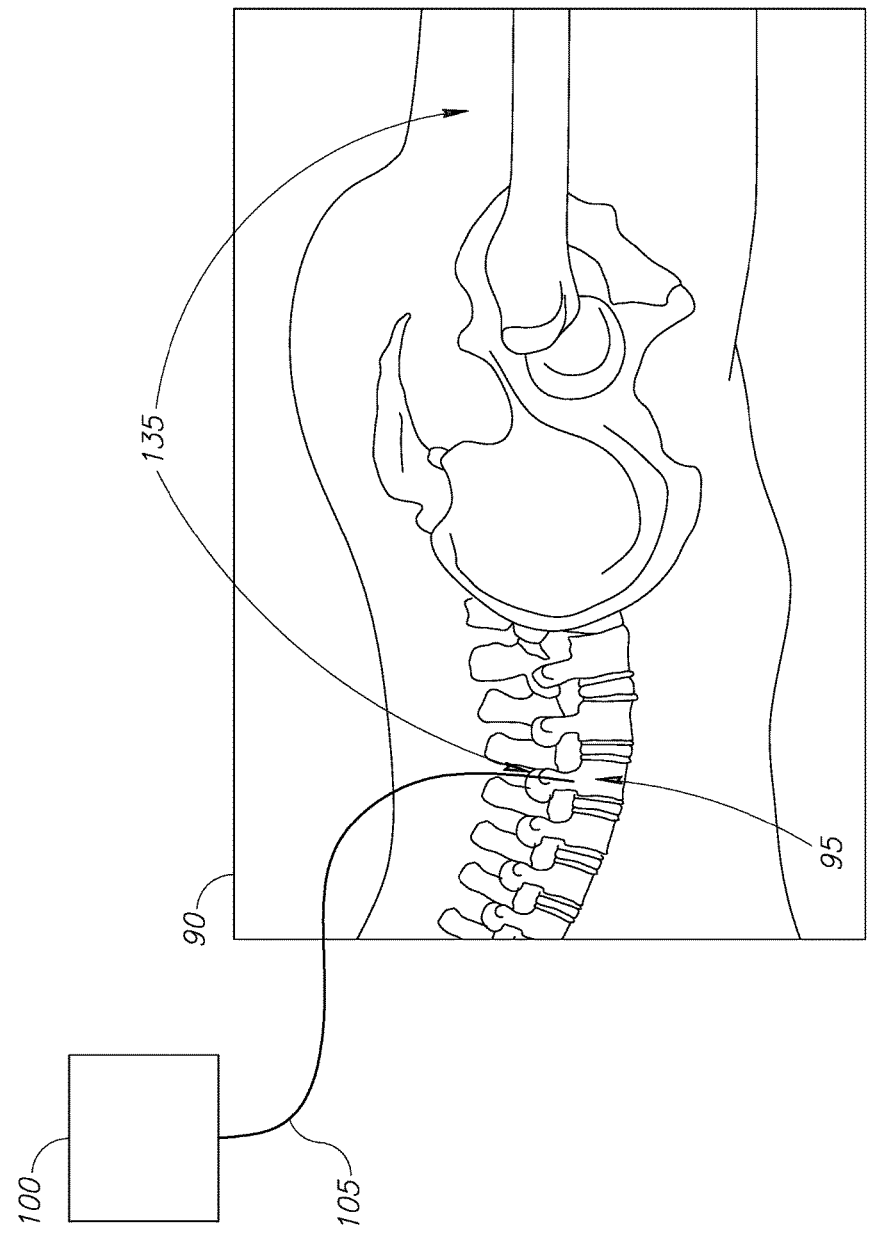

FIGS. 1A and 1B are high level schematic illustrations of treatment systems 100 for treating prostate 90 and for microsurgery at a back region 90, respectively, according to some embodiments of the invention. Treatment system 100 may be applied to treat any tissue region 90 and is configured to avoid damage to nerves and to apply nerve-preserving treatments to various body regions 90.

The surroundings of the prostate, the vertebrae (and of most other tissues and organs 90) comprise nerves 80 which are commonly injured during prior art surgical intervention, due to the difficulty in distinguishing them from surrounding tissue and/or due to other characteristics of the surgical procedure (a similar situation exists in, e.g., thyroid related operations, brain operations, spinal cord operations, tumors that contact nerves, nerve scars etc.). Advantageously, the proposed systems and methods significantly reduce or even eliminate this injury risk. Advantageously, system 100 may be used to avoid damaging nerves by applying the sensing and treatment in a sequential mode in which every treatment signal or a few treatment signals follows a sensing signal and preventing energy emission when the treatment tool is too close to specified nerves.

Treatment system 100 comprises a treatment unit 110 comprising a treatment element or tool 115 (e.g., an optical fiber or a waveguide, a plasma treatment tool, an RF electrode etc.) arranged to apply a treatment to a tissue 95, an optical stimulation unit 120 comprising an optical stimulation element 125 arranged to optically stimulate nerves 80 in tissue 95, a sensing unit 130 comprising at least one sensing element 135 (e.g., one or more electrode(s) or one or more non-contact sensor(s), which may be associated with treatment element 115 or positioned on the nerve tract or on tissue controlled by respective nerves) arranged to sense an electrical signal produced by nerves 80 in response to the optical stimulation by optical stimulation element 125 and delivered or guided along the nerves, and a control unit 140 arranged to control the application of the treatment according to the sensed electrical signal, for example in realtime and/or in a closed loop (i.e., automatically and not requiring manual intervention). In certain embodiments, sensing element(s) 135 may be deployed at a specified spatial arrangement, and/or be calibrated or tuned to cover a specified range and/or type of nerves and target tissues and thus enable a respective required monitoring requirement.

For example, in case of optical treatment, control unit 140 may control stimulation and ablation pulses parameters like intensity, pulse width, repetition rates and also the sequencing between the stimulation and treatment pulses. Control unit 140 may be arranged to immediately prevent treatment application upon sensing, by sensing unit 130, of the electrical signal produced by nerves in the tissue in response to the optical stimulation. In certain embodiments, control unit 140 may be arranged to control the optical stimulation to intersperse the optical nerve stimulation among pulses of treatment application and to immediately prevent a consequent pulse of treatment application upon detection of nerve response to the optical stimulation.

In certain embodiments, sensing unit 130 may comprise a sensing element arranged to detect movements of respective organs or tissues or other mechanical effects (e.g., a change in pressure) in the target organs or tissues.

In certain embodiments, sensing the electrical signal produced by nerves 80 in response to the optical stimulation by stimulation element 125 may be used to indicate proximity of treatment element 115 and/or the treated tissue volume 95 (and see also tissue volumes 117 in FIG. 3D) to a nerve. Control unit 140 may be arranged to immediately stop the application of the treatment in order to avoid damage to the nerves. In certain embodiments, control unit 140 may be arranged to reduce the treatment intensity below a tissue damage threshold while electrical nerve signals are sensed, or modulate the treatment intensity in inverse relation to the intensity of the sensed electrical signals or modulate the treatment pulse repetition rate.

In certain embodiments, treatment element 115 and stimulation element 125 may be integrated within a single probe 105, e.g., an optical fiber or fibers bundle (see various embodiments below). In certain embodiments, stimulation element 125 may be attached to treatment element 115 mechanically or adhesively. In certain embodiments, the tips of treatment element 115 and stimulation element 125 may be configured to have a specified spatial arrangement that enhances the safety features of system 100, as explained below. For example, a tip of stimulation element 125 may project a specified distance ahead or aside of treatment element 115 to monitor tissue regions which are advanced at.

In certain embodiments, treatment system 100 may further comprise an electrical stimulation unit 150 arranged to electrically stimulate nerves in tissue region 90 and/or treated tissue 95 via an electrical stimulation element 155 such as a stimulation electrode 155, in addition to the optical stimulation. Sensing unit 130 may be further arranged to sense an electrical signal produced by nerves in the tissue and guided along the nerves in response to the electrical stimulation. Stimulation electrode 155 may be attached to or integrated in treatment element 115 (see FIGS. 5A-5E below) or in optical stimulation element 125. In certain embodiments, electrical stimulation element 155 may be configured to stimulate a larger tissue volume than optical stimulation element 125, in order to provide long range alerts regarding the presence of nerve in the vicinity of treatment region 95 (not necessarily in the immediate treatment region 117, see below) to avoid iatrogenic nerve damage like overstretching and clamping and/or to provide an overview of the nerves in the larger area. Electrical stimulation element 155 may be associated with treatment element 115 and be configured to stimulate respective nerves to double-check optical stimulation sensing results, or for any other medical purpose. Electrical stimulation unit 150 may be arranged to stimulate nerves in a larger tissue volume 157 than optically stimulated tissue volume 127 (see FIG. 3D). For example, the electrical stimulation distance may be configured to be several millimeters or several centimeters while the optical stimulation may be configured to be in a range of tens or hundreds micrometers. Control unit 140 may be arranged to provide an alert upon the sensing of the electrical signal in response to the electrical stimulation and/or to reconfigure treatment parameters upon the sensing of the electrical signal in response to the electrical stimulation.

In certain embodiments, the treatment is light-based, and optical stimulation element 125 is configured to operate at a wavelength range that has a higher penetration coefficient in the treated tissue than a wavelength range in which optical treatment element 115 operates. In certain embodiments, the wavelength range in which optical stimulation element 125 operates is adjustable. Optical stimulation element 125 may be configured to have a larger incidence spot size than optical treatment element 115 in order to enclose treated tissue volume 117 within stimulated tissue volume 127. Treatment element 115 may be an ablative cold laser and optical stimulation element 125 may be a non-ablative laser. Treatment element 115 and optical stimulation element 125 may be lasers which are delivered through a single fiber, different fiber cores in a single fiber and/or different fibers; and differ in at least one of: their respective wavelength ranges, their respective incident spot sizes, their respective tissue penetration coefficient and their respective numerical apertures.

In certain embodiments, treatment element 115 may comprise an ablative laser, e.g., in a wavelength ranges of 1.4-1.55 µm or 1.85-2.5 µm or 9.6-11 µm as non-limiting examples (see FIGS. 2A-2D below). In certain embodiments, stimulation element 125 may comprise a laser configured not to ablate tissue, e.g., in a wavelength ranges of 1.35-1.55 µm or 1.85-2.5 µm or 9.6-11 µm as non-limiting examples or any other wavelength that provides the required safety margin with respect to the treated volume. In certain embodiments, treatment element 115 comprises a cold laser.

Figure 2A:
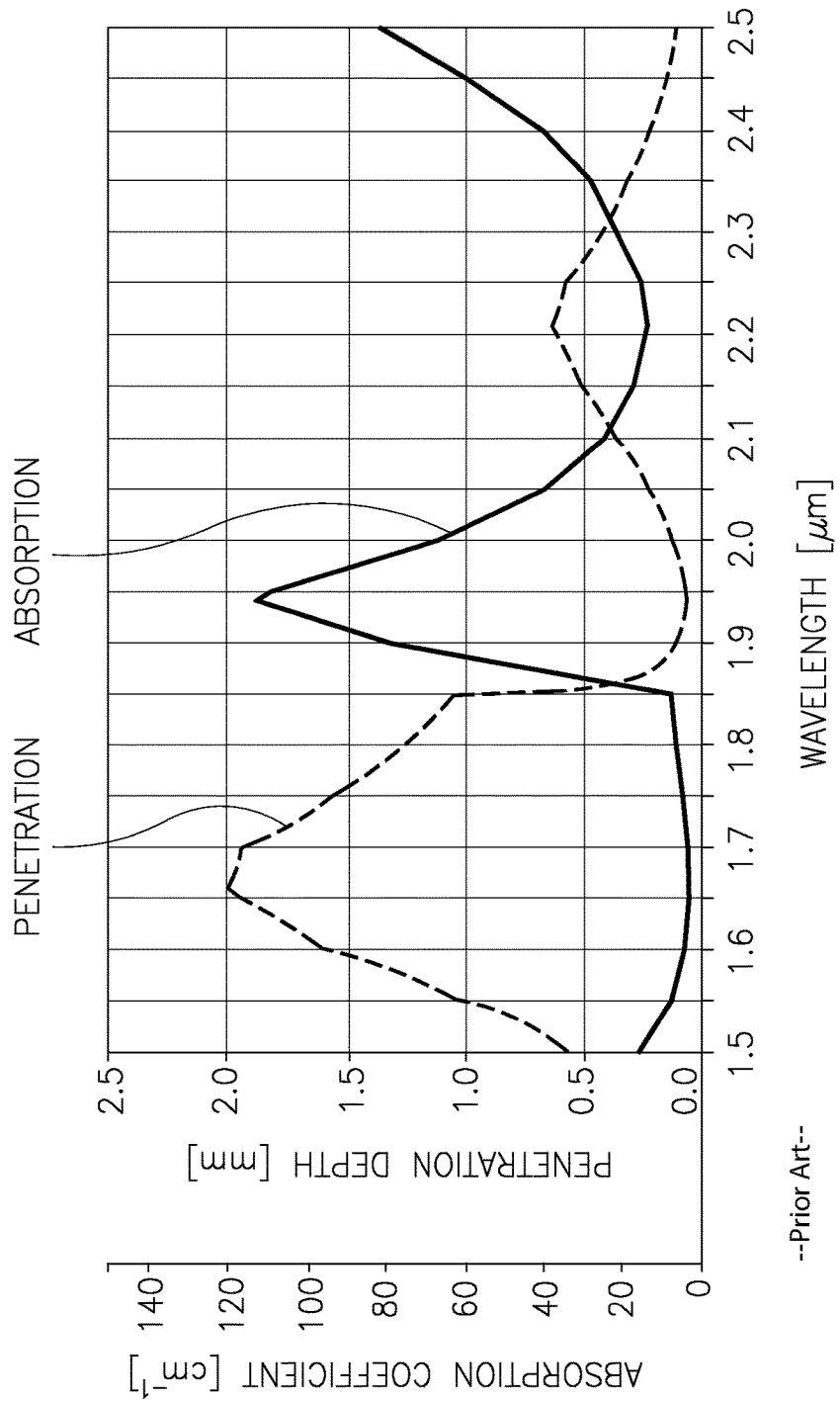
Figure 2B:
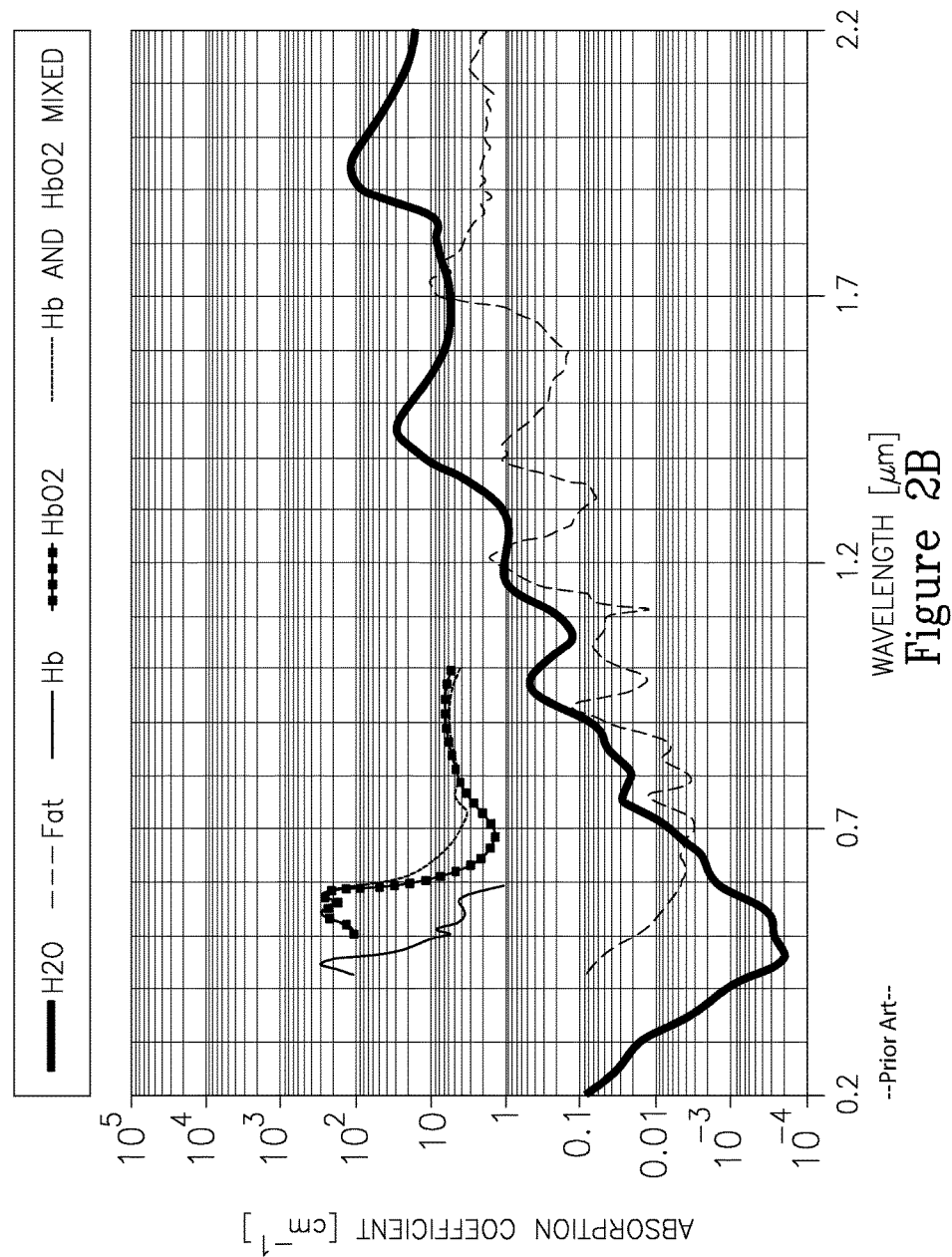
Figure 2D:
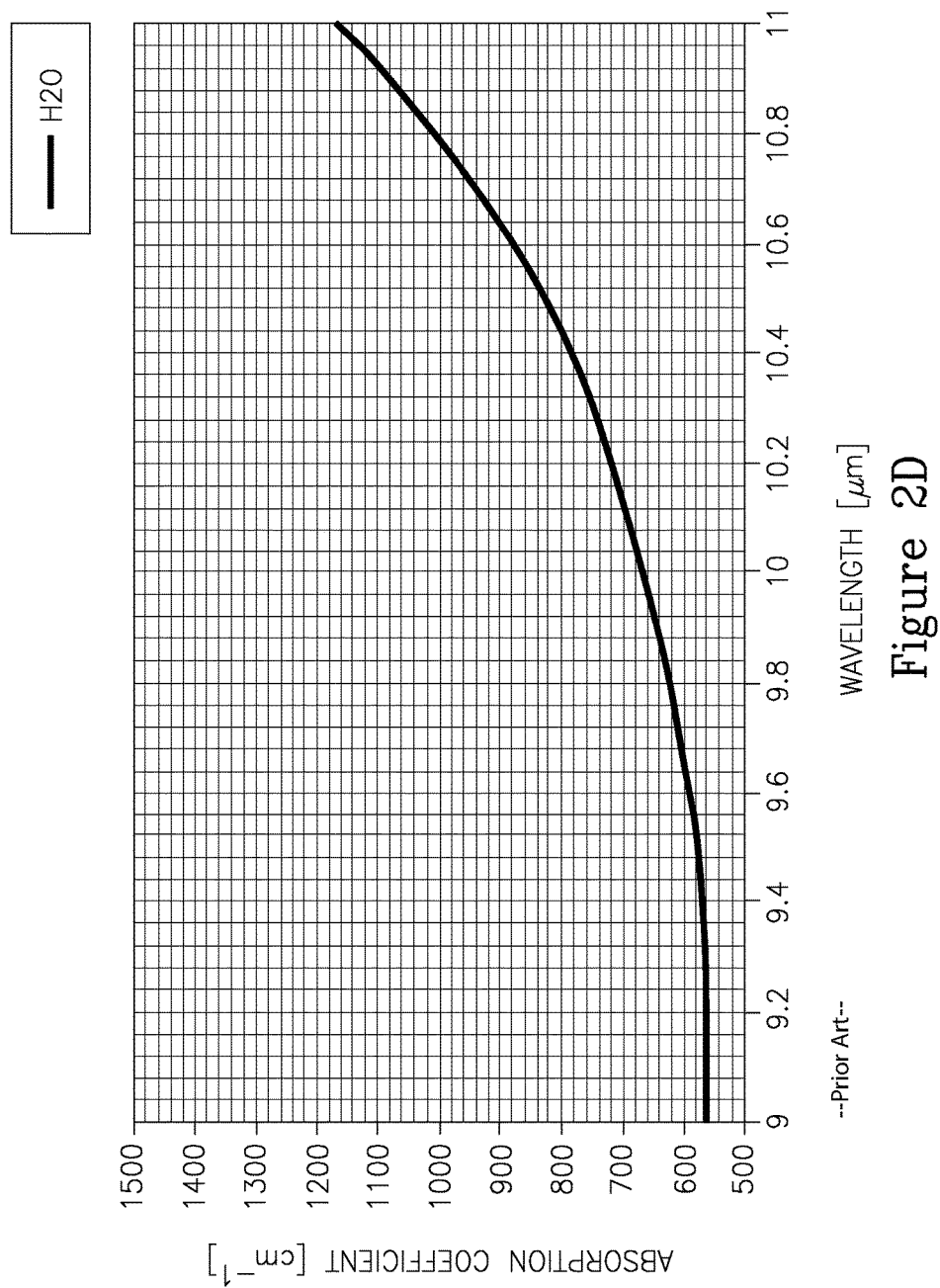

FIGS. 2A-2D are illustrations of absorption and penetration of electromagnetic radiation with respect to water, fat and blood as proxies for the absorption and penetration of electromagnetic radiation into tissue. FIG. 2A illustrates penetration and absorption through water (note that penetration and absorption are reciprocal), FIGS. 2B and 2C are illustrations of the absorption of electromagnetic radiation of various tissue and blood components, that may be used to adapt treatment and stimulation wavelength ranges with respect to specific treatment regions 95. FIGS. 2B and 2C illustrate absorption by water ($H_2O$, similar to FIG. 2A), fat, hemoglobin (Hb), oxidized hemoglobin ($HbO_2$), and mixed oxidized and non-oxidized hemoglobin (Hb and $HbO_2$ mixed) at two wavelength ranges (0.2-2.2 µm and 0.1-12 µm, respectively). FIG. 2D illustrates the dependency of the absorption coefficient in water for a wavelengths between 9-11 µm. FIG. 2D is depicted in a linear scale (compare to FIG. 2C) in order to illustrate the wavelength dependency of the absorption coefficient which is utilized to achieve stimulation volumes 127 which are larger than ablation volumes 117 (see FIG. 3D).

As is clear from FIGS. 2A-2D, the wavelength of the ablative laser may be selected to have high absorption of radiation, while the wavelength of the stimulation laser may be selected to have higher penetration. For example, the wavelength of the ablative laser may be selected as 1.94 µm and the wavelength of the stimulation laser may be selected as 2.1 µm. This example is non-limiting, as the specific wavelengths may be selected with respect to specific treatment requirements and stimulation requirements, and may even be dynamically changed during the treatment. Advantageously, such selection combines effective small volume ablation by treatment element 115 (requiring a high absorption coefficient) with an effective larger stimulation volume by stimulation element 125 (requiring a higher penetration coefficient). The wavelengths may be adjusted to control the spatial extent of the treatment, the spatial extent of the stimulation, and the ratio of treatment to stimulation spatial extents. The wavelengths may be selected with respect to experimental data relating to specified tissues.

Figure 3A:
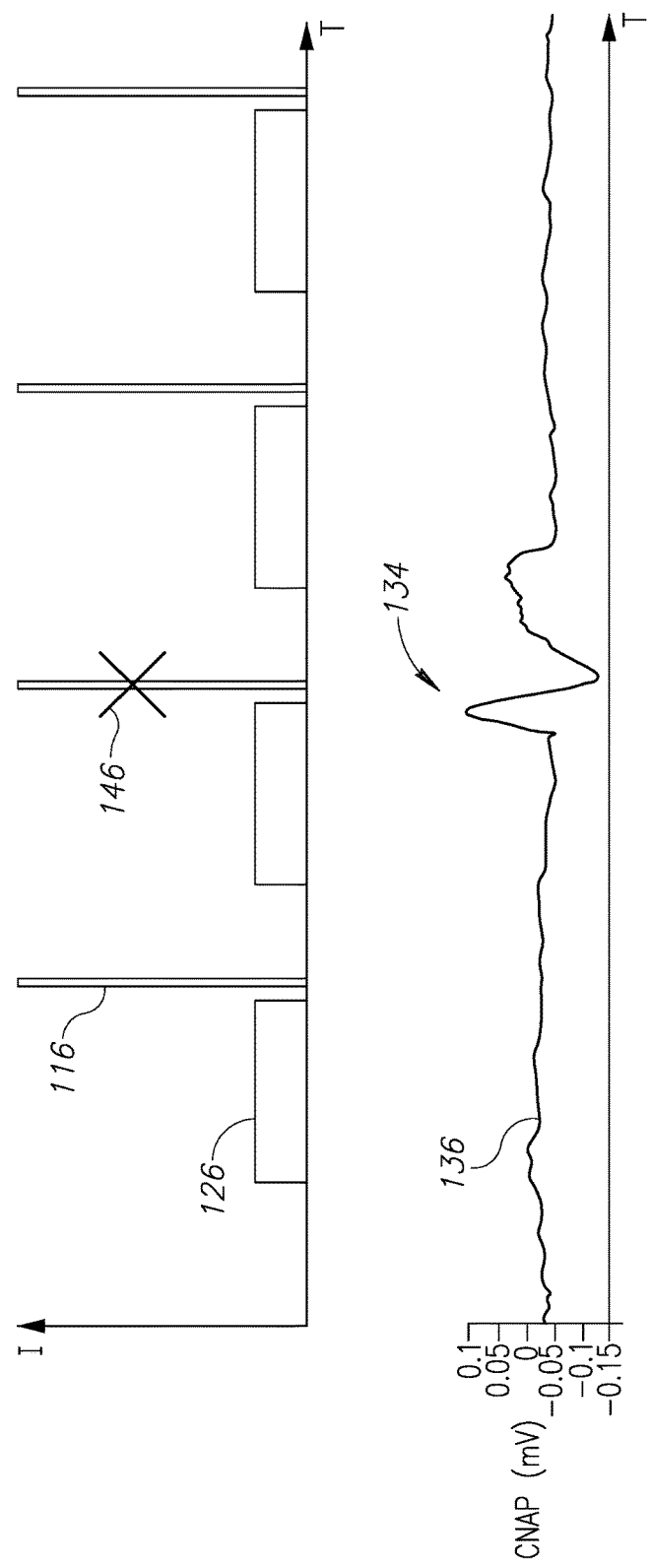
FIG. 3A is a schematic high level illustration of a treatment signal delivered by treatment element such as an ablative laser, a stimulation signal delivered by stimulation element such as a non-ablative laser and a sensing signal as sensed by sensing electrode, according to some embodiments of the invention.

FIG. 3A is a schematic high level illustration of a treatment signal 116 delivered by treatment element 115 such as an ablative laser, an optical stimulation signal 126 delivered by stimulation element 125 such as a non-ablative laser and a sensing signal 136 as sensed by sensing electrode 135, according to some embodiments of the invention. Signals 116, 126 and 136 are illustrated with a common time scale. Upon detection of electrical signal 134 in sensing signal 136 (e.g., resulting from the preceding stimulation signal 126, in the non-limiting illustrated case, a pulse), treatment signal 116 may be not applied (e.g., in the non-limiting illustrated case, a next scheduled pulse may be cancelled 146) to avoid damage to the stimulated nerves. In certain embodiments, the treatment signal 116 may be resumed when no electrical signal 134 is detected. Optical stimulation signal 126 may be delivered continuously during the treatment (e.g., as a continuous train of pulses) in order to monitor the proximity of treatment element 115 and/or treated tissue 95 to nerves 80, so that sensing signal 136 may be monitored continuously. Sensing signal 136 may be time correlated with stimulation signal 126 to enhance the signal to noise and improve the nerve detection reliability. In certain embodiments, stimulation signal 126 may be arranged to precede treatment signal 116 by a time period that enables cancelling 146 of the consecutive treatment signal 116 in case of nerve detection.

In certain embodiments, treatment signal 116 (e.g., an ablation pulse) may be selected to be shorter than 200 nanoseconds (and may then be regarded as being "cold", i.e., as not heating the tissue excessively) or to be several hundred μs long, as in common surgical lasers which heat the treated tissue to some extent (in addition to the applied ablation effect). The pulse width depends on the laser wavelength, the pulse energy, spot size, etc., and may be configured to enable efficient treatment effectively controlled by the closed loop control circuit involving the optical stimulation.

In certain embodiments, the pulse width of stimulation signal 126 may be configured according to specific treatment regions and profiles and may be flexibly configured during operation with respect to the application of treatment signal 116. The pulse fluence (energy/cm$^2$) may selected to be below the thermal damage threshold (few Joules/cm$^2$) and the pulse width may be selected to be shorter than the thermal relaxation time to avoid heat dissipation. Practically, the pulse width of stimulation signal 126 may be selected to be several hundred μs or a few milliseconds long. The period between treatment signal 116 and stimulation signal 126 is selected to enable efficient detection of detection signal 134 with respect to the nerve conduction velocity and the distance of sensing electrode 135 from the stimulation point.

It is noted that the time period between stimulation pulses 126 and treatment pulses 116 may be selected to accommodate the time required for the nerves to respond (depending on nerve type and location of electrode 135). In certain embodiments, stimulation signal 126 and/or treatment signal 116 may be pulsed, with stimulation pulses preceding treatment pulses. For example, the pulse frequency may be 400 Hz, 10 Hz, 1 Hz. In certain embodiments, stimulation signal 126 may comprise a single pulse or be in any range between a very low frequency (<<1 Hz) and the limit of nerve response (several tens of Hz or a few hundred Hz). The stimulation frequency may be selected according to respective stimulated nerves characteristics like refractoriness and conduction speeds (e.g., in the range 0.5-120 meters per second, or, depending on the nerve type. 0.5-3 m/s, 3-30 m/s, 30-80 m/s, 80-120 m/s) and with respect to the distance of sensing electrode 135 from treatment location 95 (e.g., few millimeters in case of close electrode positioning, several centimeters in case of farther electrode locations and up to tens of centimeters in case of sensing electrodes positioned remotely from the location of stimulation). The nerve diameters which are associated with each conduction speed range may also be taken into account when selecting the temporal pattern of the optical stimulation and optical stimulation volume 127. Table 1 exemplifies a non-limiting relation between an arithmetic limit of the optical stimulation rate due to the nerve conduction speed and the location of sensing electrode 135, which is derived from simple speed versus distance consideration. For nerves with high conduction speed the actual stimulation rate may be limited by the absolute refractory period.

TABLE 1

An exemplary relation between an arithmetic limit of optical stimulation rate, the nerve conduction speed and the location of the sensing electrode.

| Distance to sensing electrode | Nerve Conduction speed | | | |
|---|---|---|---|---|
| | 0.5 m/s | | 120 m/s | |
| | Excitation travelling time | Arithmetic limit of Stimulation rate | Excitation travelling time | Arithmetic limit of Stimulation rate |
| 5 cm | 100 ms | 10 Hz | 417 μs | 2.4 kHz |
| 10 cm | 200 ms | 5 Hz | 834 μs | 1.2 kHz |
| 15 cm | 300 ms | 3.3 Hz | 1.25 ms | 800 Hz |

In certain embodiments, several stimulations may be performed in each location to enhance the signal to noise ratio and to differentiate between the stimulated action potential from the sporadic/parasitic/spontaneous action potentials.

In certain embodiments, stimulation signal 126 may be delivered at specified locations with respect to a pulse train of treatment signal 116, or be itself delivered as a pulse train with a frequency determined with respect to the treatment pulse train. A ratio between the number of stimulation pulses 126 and treatment pulses 116 may be selected with respect to nerve density in tissue region 90 and/or with respect to other anatomical parameters and/or with respect to the ratio between the treatment pulse penetration volume and stimulation pulse penetration volume, ahead of treatment or during treatment, with respect to the distance of the treatment area to the nerve and may be adjustably configured in realtime. Optical stimulation signal 126 may be adapted and adjusted in realtime with respect to results of the electrical stimulation.

Figure 5A:
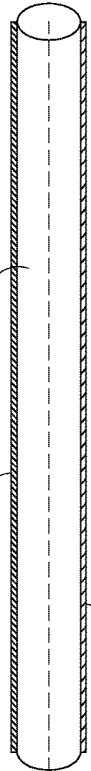
FIGS. 5A-5E are high level schematic illustrations of configurations of the treatment fiber, with the treatment element and the stimulation element, optional electric stimulation element and the sensing electrode, according to some embodiments of the invention.
Figure 5B:
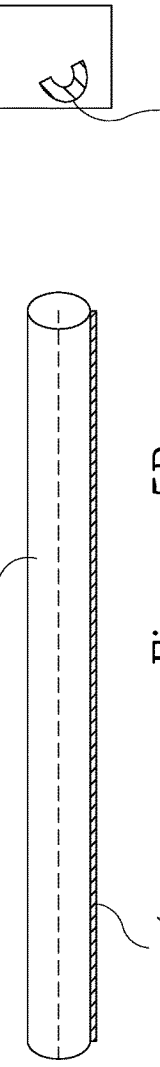
Figure 5C:
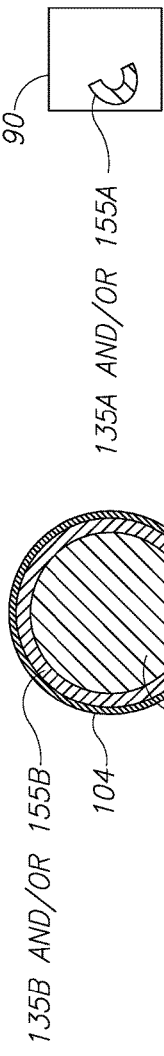
Figure 5D:
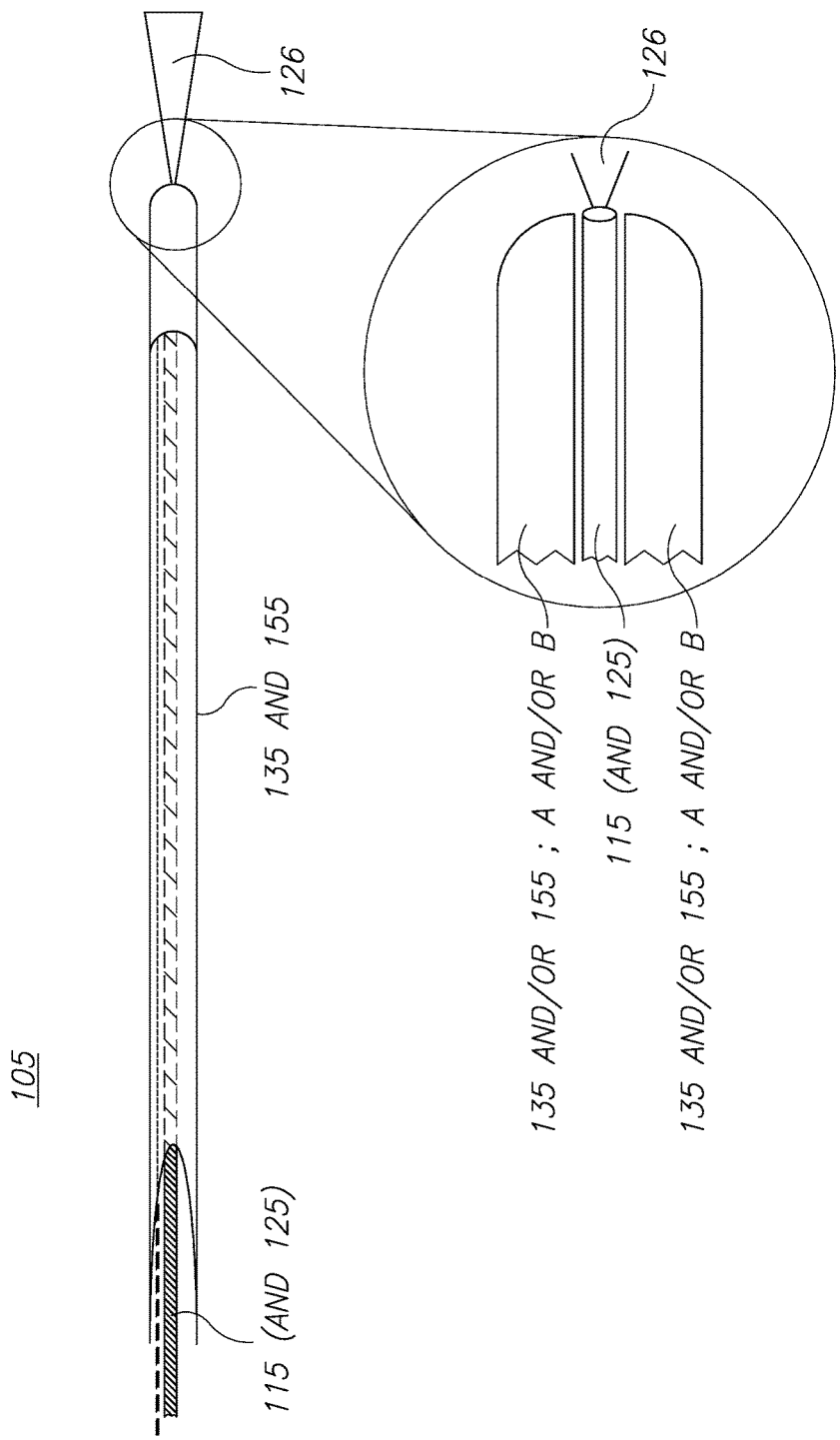
Figure 5E:
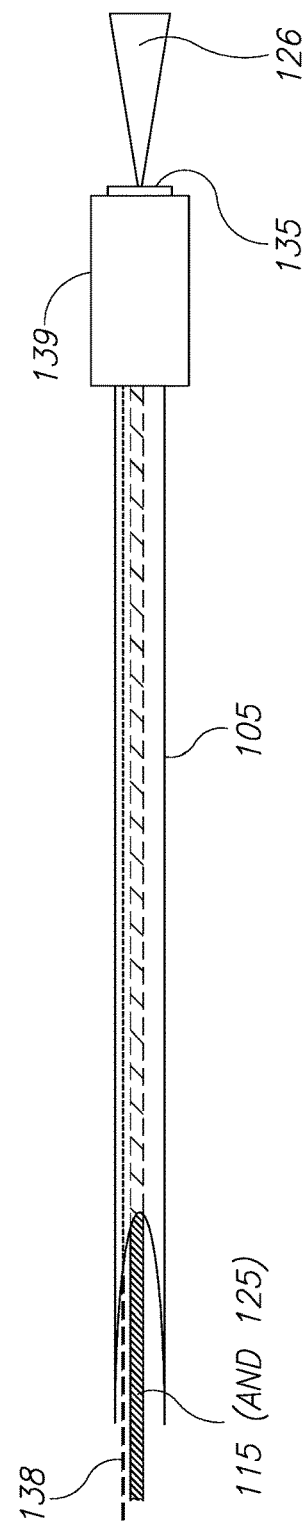

In certain embodiments, particularly ones in which nerves having a low conduction speed are stimulated, the measuring distance may be kept small by using noncontact electrophysiological sensor(s) based on either electrical field sensing (like for example, capacitive coupled electrodes) or magnetic field sensing (like for example SQUID sensor(s)) as sensing electrode 135 or remote sensor 135 (see FIG. 5E). In such application, sensing the stimulated action potential may be carried remotely by non-contact sensor 135 that may be attached to treatment element 115, to stimulation element 125 or be placed independently of these elements.

Figure 3B:
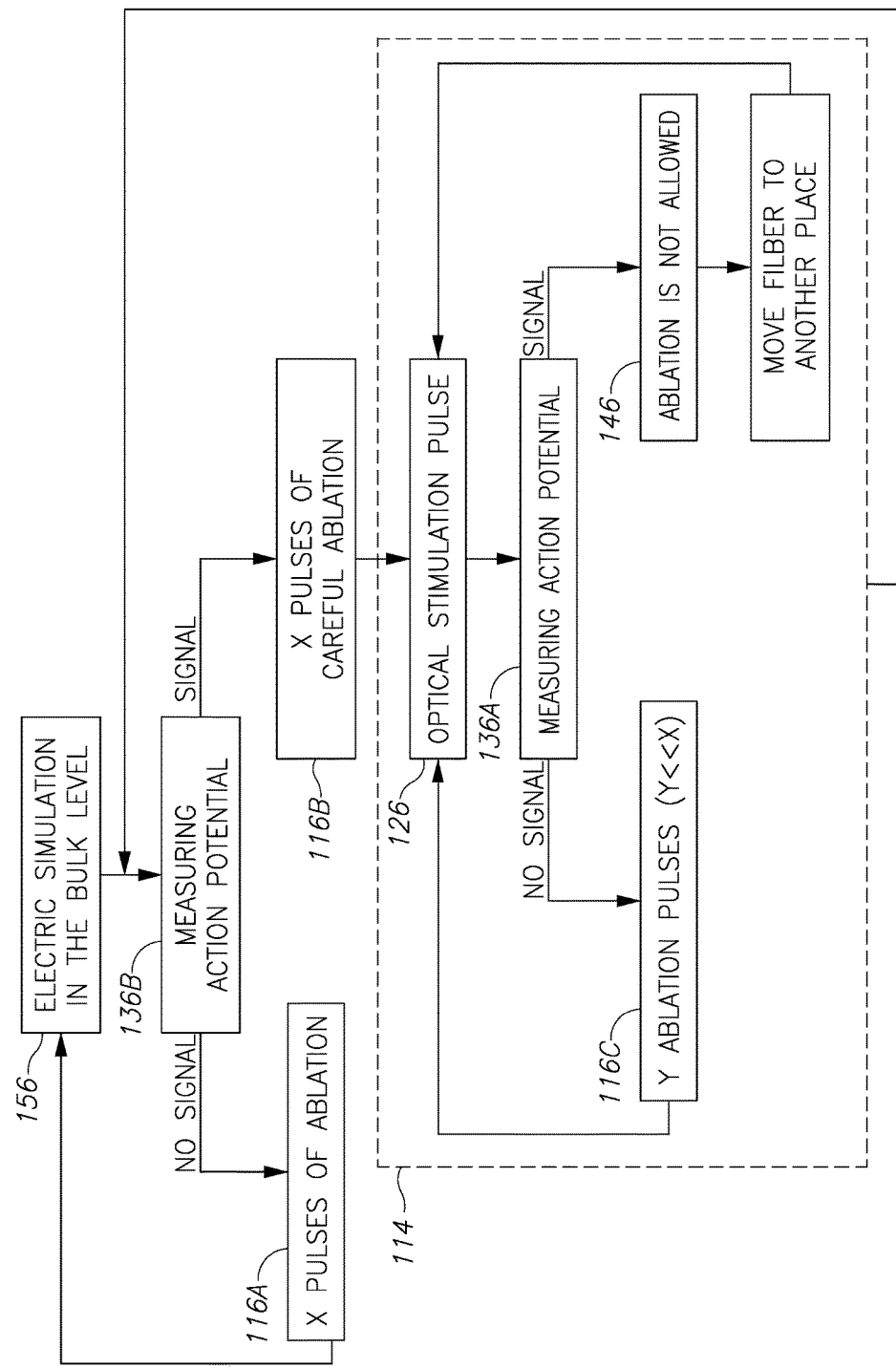
FIGS. 3B and 3C are high level schematic flowcharts illustrating optical and optionally electric stimulation in a closed loop control of a treatment tool, according to some embodiments of the invention.
Figure 3C:
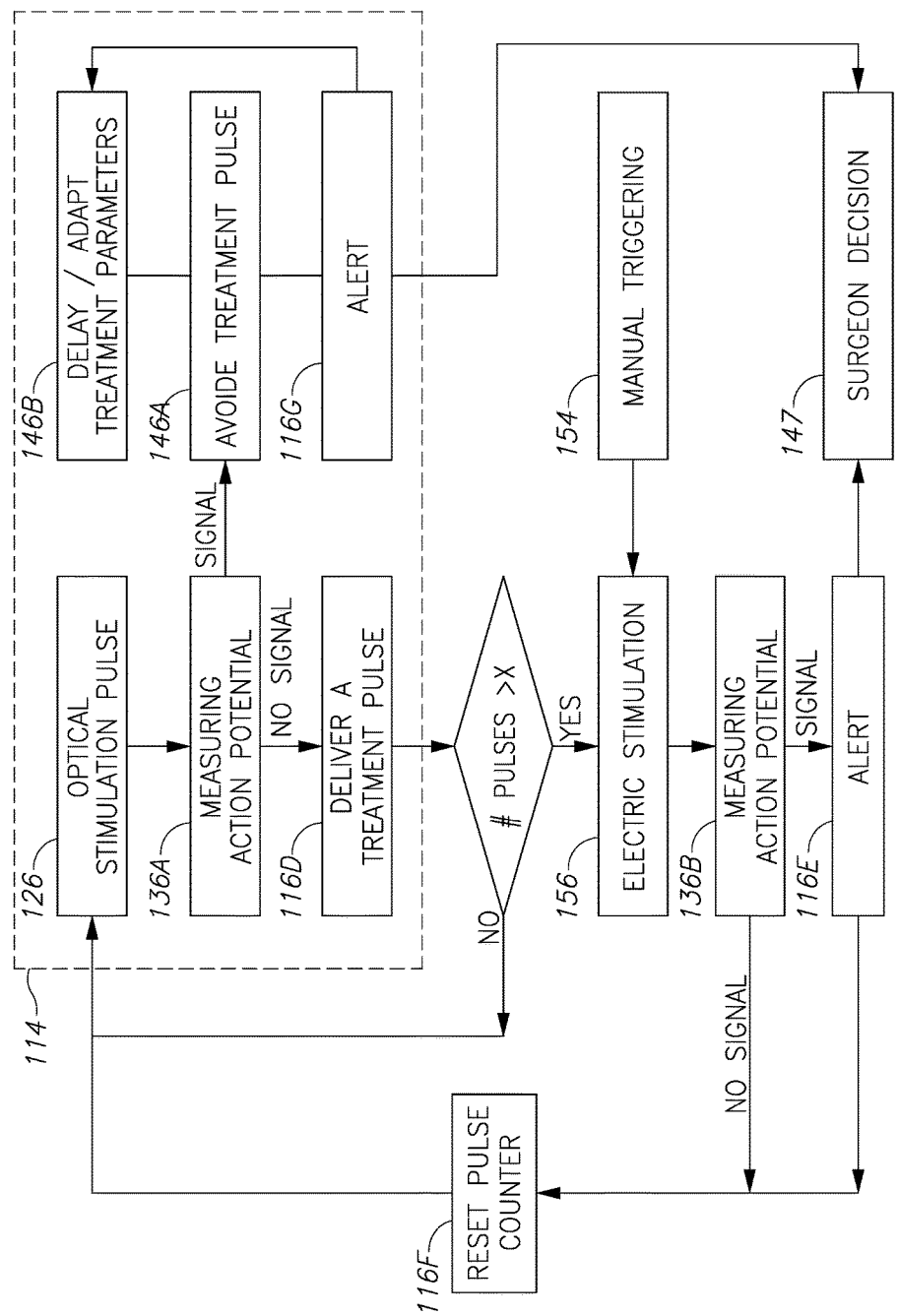

FIGS. 3B and 3C are high level schematic flowcharts illustrating optical and optionally electric stimulation in a closed loop control of a treatment tool, according to some embodiments of the invention. In certain embodiments, optical stimulation may be used for controlling the treatment tool in a closed loop 114. FIGS. 3B and 3C illustrate optical treatment as a non-limiting example; similar principles may be applied to other types of treatment elements 115. Closed control loop 114 comprises optical stimulation pulse 126 followed by a measurement of resulting action potential(s) 136A. In case no signal (i.e., no stimulation) has been detected, ablation pulse(s) 116C, 116D may be applied (e.g., a train of Y pulses 116C, Y selected for the actual ablation to be well within stimulation volume 127—FIG. 3B, or a treatment pulse 116D of any kind which is contained within stimulation volume 127—FIG. 3C). In case a signal (i.e., stimulation) has been detected, ablation may be prevented 146 as a safety mechanism, implementing a "safe knife" configuration of the ablative tool (treatment element 115). The practitioner may move the tip of treatment element 115 to a safer location, as indicated by lack of stimulation (i.e., ablated tissue volume 117 does not include a target nerve). Closed loop 114 may be implemented without manual intervention, allowing it to be fast and limited only by the respective nerve response rate.

The control algorithm may be applied with respect to several sensing elements 135, and with respect to their specific locations. Calculations of required response time may also be differentiated with respect to several sensing elements 135.

Optional electric stimulation may be implemented in addition to the optical stimulation and may be used to check for nerves within a larger region 157 than optical stimulation volume 127. Advantageously, such bulk stimulation 156 may be used to map nerves which are further away from the treatment location as an indication of tissue being approached by treatment element 115 but is currently not treated. Upon electric stimulation 156, action potentials are measured 136B.

In case no signal (i.e., no stimulation) has been detected, ablation pulse(s) 116A may be applied (e.g., a train of X pulses 116A, X selected with respect to the geometrical relations among volumes 117, 127, 157—FIG. 3B) and/or a pulse counter may be reset 116F, and X pulses may be applied one by one upon no signal detection following optical stimulation (FIG. 3C) or ablation pulses may be applied as by the surgeon decision.

In case a signal (i.e., stimulation) has been detected as result of the electric stimulation, either treatment may be modified (e.g., into X pulses of careful ablation 116B, i.e., having lower energy, slower treatment rate, delay the next pulse—FIGS. 3B, 3C) or an alert 116E may be created and ablation continued only upon lack of signal detection after optical stimulation 126 (FIG. 3C).

In certain embodiments (FIG. 3C), upon measuring action potential 136A, a treatment pulse is avoided 146A, and alert 116G is created and delivered to the surgeon, and treatment parameters may be adapted or the next treatment pulse may be delayed 146B. Upon surgeon's decision 147, further treatment parameters and treatment location may be modified. The changes in treatment parameters may be determined with respect to treatment type and location, and take into account the refractory period of the respective nerves.

volume 117 per laser treatment pulse to ensure safety margins. Volume size adjustment may be achieved using different wavelengths for stimulation element 125 and treatment element 115 which are selected such that the penetration depth of stimulation signal 126 (e.g., stimulation pulse) is larger than the penetration depth of treatment signal 116 (e.g., ablation pulse). In certain embodiments, electrically stimulated tissue volume 157 may be much larger than optically stimulated tissue volume 127.

The size of the safety margin may be controlled by the difference of the tissue absorption coefficients of the two wavelengths. In general, ablation volume 117 may be characterized by a depth $d_1$ and volume $v_1$ which are determined by wavelength $\lambda_1$ and numerical aperture $\psi_1$ as well as by the spot size on the tissue (derived e.g., from the fiber diameter and the distance to the tissue) while optical stimulation volume 127 may be characterized by a depth $d_2$ and volume $v_2$ which are determined by wavelength $\lambda_2$ and numerical aperture $\psi_2$, as well as by the spot size on the tissue (which may be different than for the treated volume). Without being bound by theory, the scattering coefficient also affects the respective volume. The scattering coefficient which is wavelength dependent and the entrance spot size, in addition to the numerical aperture, affect not only the volume width but also the volume depth d. Therefore, two fibers with different core diameters or using a concentric dual core optical fiber in which the ablation laser propagates in the inner core and the stimulation propagates in the inner and external cores can result in the required differentiation between volumes 117, 127. These and other parameters may be selected so as to provide a safety margin for the operator of treatment element 115 and spare nerves in the operation scene. Table 2 presents non-limiting examples for approximate optically stimulated tissues volumes with respect to the selected wavelength and the spot size on the tissue. The presented approximation is geometrical and disregards optical effects which may be taken into account in more detailed calculations. Thus, the optical stimulation wavelength may be selected to provide a stimulated tissue volume which provides sufficient safety margins with respect to the treated tissue volume (which may be calculated in a similar manner from the absorption curves—see e.g., FIG. 2A).

TABLE 2

An exemplary determination of approximate optically stimulated tissue volumes with respect to the selected wavelength and fiber aperture.

| Wavelength | Penetration depth in water | Spot size on the tissue | | |
|---|---|---|---|---|
| | | 50 μm | 100 μm | 250 μm |
| 1.875 μm | 222 μm | $0.44 \cdot 10^6 (\mu m)^3$ | $1.74 \cdot 10^6 (\mu m)^3$ | $10.88 \cdot 10^6 (\mu m)^3$ |
| 2.22 μm | 630 μm | $1.24 \cdot 10^6 (\mu m)^3$ | $4.94 \cdot 10^6 (\mu m)^3$ | $30.88 \cdot 10^6 (\mu m)^3$ |
| 2.30 μm | 435 μm | $0.85 \cdot 10^6 (\mu m)^3$ | $3.41 \cdot 10^6 (\mu m)^3$ | $21.31 \cdot 10^6 (\mu m)^3$ |

In certain embodiments, electric stimulation 156 may be manually triggered 154 in addition or in place of scheduled electric stimulation.

Figure 3D:
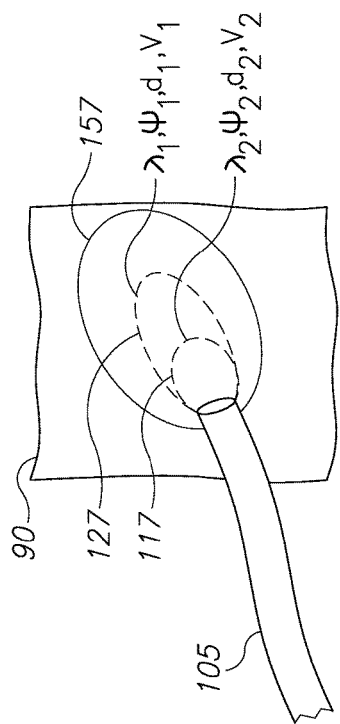
FIG. 3D schematically illustrates tissue volumes which are affected, respectively, by the treatment and by the stimulation elements, according to some embodiments of the invention.

FIG. 3D schematically illustrates tissue volumes 117, 127, 157 which are affected, respectively, by treatment and stimulation elements 115, 125, 155 (respectively), according to some embodiments of the invention. In certain embodiments, optically stimulated tissue volume 127 (e.g., per laser pulse 126) at least overlaps ablation volume 117 (e.g., per laser ablation pulse 146). In certain embodiments, optical stimulation volume 127 per laser pulse is larger than ablation The safety margin may be defined per specific applications by pre-definition of the laser's wavelengths and/or fiber aperture and/or numerical aperture. For example, in neuro-oncology surgery where oncology safety is crucial the safety margin may be selected to be low (e.g., 100 μm around treatment region 117). In contrast, in orthopedic surgery, where the nerve bundle is large and visually recognized the safety margin may be selected to be higher (e.g., 500 μm around treatment region 117).

In certain embodiments, at least one of stimulation element 125 and treatment element 115 are tunable to enable adjustment of the safety margins for specific applications (see the effect of changing the wavelength on the stimulation volume in Table 2). This safety margins may be planned to withstand ablation laser variations such as pulse energy, pulse width etc. In certain embodiments, the wavelength of the stimulation ($\lambda_2$) may be adjusted to control the size of the stimulation volume ($v_2$) over the tissue penetration coefficient (see FIGS. 2A, 2B). In certain embodiments, elements 115 and/or 125 may be configured to have specific spatial relationships that further define volumes $v_1$, $v_2$.

For example, different treatment volumes $v_1$ associated with different common lasers are presented in Table 3. By adapting wavelength $\lambda_2$ of stimulation signal 126 according to known penetration characteristics (e.g., FIGS. 2A, 2B), the stimulated volume may be adjusted. The illustrated range of beam widths ($d_1$=50 μm to 1 mm) is applicable to the beam widths ($d_2$) of stimulation signal 126 as well (beam width being considered e.g. as the diameter that includes two thirds of the beam energy). Penetration coefficients of stimulation signal 126 may be adjusted e.g., in a $\mu_a$ range of 10-1000 1/cm.

TABLE 3

Treatment volume for common laser types

| Type of laser | Wavelength $\lambda_1$ (μm) | Penetration coefficient $\mu_a$ (1/cm) | Penetration depth (μm) | Treatment volume $v_1$ (μm)$^3$ | |
|---|---|---|---|---|---|
| | | | | $d_1$ = 50 μm | $d_1$ = 1 mm |
| Holmium | 2.1 | 26 | 385 | $7.55 \cdot 10^5$ | $3.02 \cdot 10^8$ |
| Thulium fiber laser | 1.94 | 114 | 88 | $1.72 \cdot 10^5$ | $6.89 \cdot 10^7$ |
| Thulium solid state | 2.01 | 62 | 161 | $3.17 \cdot 10^5$ | $1.27 \cdot 10^8$ |
| $CO_2$ | 10.6 | 890 | 11 | $2.21 \cdot 10^4$ | $8.82 \cdot 10^6$ |

In certain embodiments, the safety margins may be tuned to withstand the tool manual or robotic movement during the time period between stimulation and ablation pulses (126 and 116 respectively). In applications of fast repetition rate treatment laser, such as, for example, femtosecond laser as treatment element 115, stimulation signal 126 may be emitted every plurality of femtosecond pulses to allow sufficient time for the nerves to respond to the stimulation (nerve stimulation rates typically range up to a few tens or hundreds Hz) and enable both effective ablation by the femtosecond laser and maintaining the required safety margin.

In certain embodiments, the two volumes (stimulation and treatment volumes 127, 117, respectively) may be spatially adjusted to compensate for movements or expected movements of treatment element 115. In certain embodiments, treatment and stimulation elements 115, 125 may have the same wavelength or the same penetration coefficient and the safety margin may be defined by setting of the operation parameters of any of elements 115, 125 (e.g., the ablation laser and/or the stimulation laser).

In certain embodiments, sensing element 135 may be configured to sense excitation of certain nerves and not others. Differentiation between nerves may be carried out anatomically, via stimulation parameters and/or via sensing parameters. Treatment aims may determine which nerves are sensed. In prostatectomy, for example, nerves that innervate the prostate itself, which is to be removed during the operation, may be severed, while nerve that should function normally after the operation may be preserved. Nerve identification may be carried out anatomically by placing electrode 135 on the appropriate nerve(s) (or on nerves of target organs) and not on nerves which are allowed to be severed. Nerve identification may be carried out using nerve mapping (e.g., electrically) prior or during the operation. Nerve differentiation may be carried out by adapting the stimulation efficiency, e.g., with respect to nerve structure (e.g., myelinated and non-myelinated nerves may be stimulated differently, bundled and non-bundled nerves may be stimulated differently, nerves in close proximity of blood vessels may be stimulated differently than other nerves). As an example for nerve differentiation by optical stimulation, Wells et al. ("Pulsed laser versus electrical energy for peripheral nerve stimulation", Journal of Neuroscience Methods 163 (2007) 326-337) demonstrate the validity of optical nerve stimulation. In certain embodiments, differences in the dependency of the penetration coefficients on the wavelengths (FIG. 2B) may be used to determined stimulation volume $v_2$ with respect to different types of tissue and to different types of nerves. Based on Wells et al.'s data, system 100 may be configured to have an effective nerve stimulation beyond the treated volume (see, e.g., the penetration depth data in FIG. 8 in Wells et al.).

Advantageously, the proposed systems, devices and methods overcome the common risk of nerve damage in many surgical procedures. Damage to nerves of the central or peripheral nervous systems harms the patient quality of life and may cause temporary or permanent palsy or sensing inability. The known methods map nerve structures electrically, and, therefore, they are limited by the coarse localization nature of electric measurements and are restricted to delayed sensing due to the noise of the stimulation pulse. Therefore, known methods do not implemented a closed loop control. The optical stimulation and laser based treatment disclosed herein, localize the stimulation and treatment to the penetration volumes and brings the resolution to sub-millimeter ranges. This high resolution optical stimulation enables immediate sensing without a time delay. This in turn enables real time closed loop control of treatment application by the sensing measurements of nerve excitation. The continuous measurement that is achieved in the present invention which its measurement rate is limited by the tissue response (mainly by the refractoriness) reflects the effectiveness of high resolution optical stimulation and provides a significant advantage with respect to known open loop electrical stimulation based applications which measures manually from time to time along the operation and includes the surgeon in the control loop via a visual or auditory signal. The described systems and methods may be applied to a wide variety of surgical procedures, for example, surgical cutting, tissue ablation, excision and coagulation and enhance the treatment safety by avoiding nerves damage. In certain embodiments, the present invention teaches nerve detection by laser nerve stimulation accompanied by electrical detection of electrophysiological signals. Treatment system 100 may be used with respect to various treatment tools and technologies which may be implemented by treatment unit 110, such as radiofrequency electromagnetic radiation (RF) or microwave radiation (e.g., cutting devices; mono-polar, unipolar, bipolar RF), mechanical procedures (cold cutting, e.g., by scalpel or scissors), electro-optical treatment (e.g., lasers in various operation modes—pulsed or continuous, laser in flash vaporization mode, a femto-second laser etc.), plasma treatment, electrocautery (electrical heat treatment), ultrasound (e.g., cutting tools) and so forth. System 100 may be arranged to avoid mechanical injuries, heat injuries etc. by appropriate tuning of sensing and damage thresholds of sensing unit 130 and control unit 140, respectively.

For example, the following are possible non-limiting examples for medical applications for the proposed systems and methods. In ear, nose, and throat (ENT) medicine, e.g., vocal cords cancer, laryngology, facial surgeries, carotid endarterectomy and carotid surgery in general, cricopharyngeal myotomy, excision of Zenker's diverticulum, hemithyroidectomy, neck biopsy, neck dissection, parathyroidectomy, partial laryngectomy, substernal goiter, thyroidectomy and thyroid surgery in general, basal cell cancer in the ear canal, melanoma in the ear canal, adenoid cystic, adenocarcinoma, acoustic neuroma, parotid surgery etc. In urology, e.g., benign prostatic hyperplasia (BPH), prostate cancer—radical prostatectomy, bladder cancer, peyronie, perineal anal plastic during paedriatric surgery, etc. In neurosurgery—accurate tissue incision and avoiding damaging to the nerves in the central nervous system, functional neurosurgery. In orthopedics—scoliosis, screw placement during placement of opened and/or percutaneous pedicle screw, minimal invasive surgery of intervertebral discs and general orthopedics surgeries. Additional applications are in the fields of heart thoracic surgery, mediastinoscopy, vascular surgery, thoracoabdominal aorta aneurysm surgery, pain treatment procedures, recognition of nerves in general surgeries and any other procedure that may benefit from avoiding damage to the nerves in the peripheral nervous system.

Figure 4A:
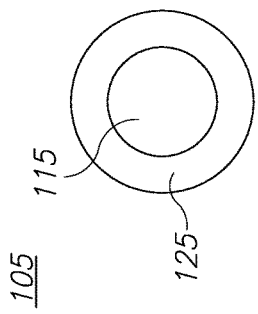
FIGS. 4A-4E are high level schematic illustrations of element configurations, according to some embodiments of the invention.

FIGS. 4A-4E are high level schematic illustrations of element configurations, according to some embodiments of the invention. FIG. 4A illustrates certain embodiments, in which the ablative laser as treatment element 115 and the non-ablative laser as stimulation element 125 are delivered through a single fiber 105. For example, elements 115, 125 may be arranged concentrically, with stimulation element 125 comprising both layers (inner and outer core) or one layer (e.g., the outer core) while treatment element 115 comprises the inner core. In another example, illustrated in FIG. 4B, elements 115, 125 may be the same fiber 105, with respective illumination 115, 125 directed into fiber or a waveguide, e.g., via a beam combiner 102. Treatment element 115 and simulation element 125 thus share an optical path through fiber 105 and have a same or a similar numerical aperture ψ, and beam spread 103.

Figure 4B:
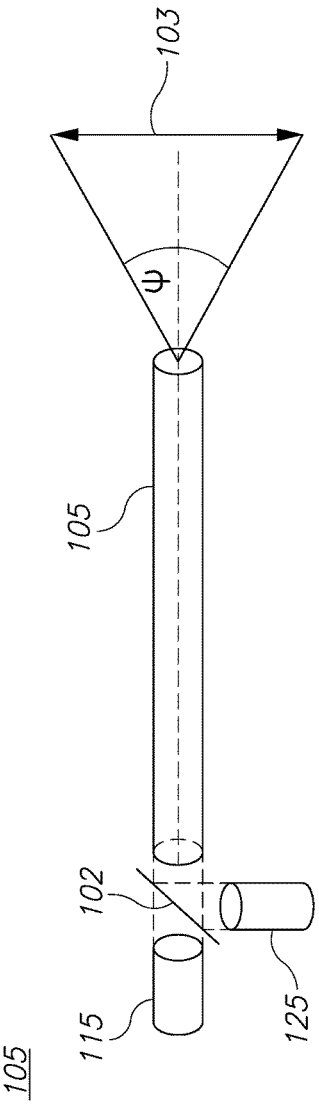
Figure 4C:
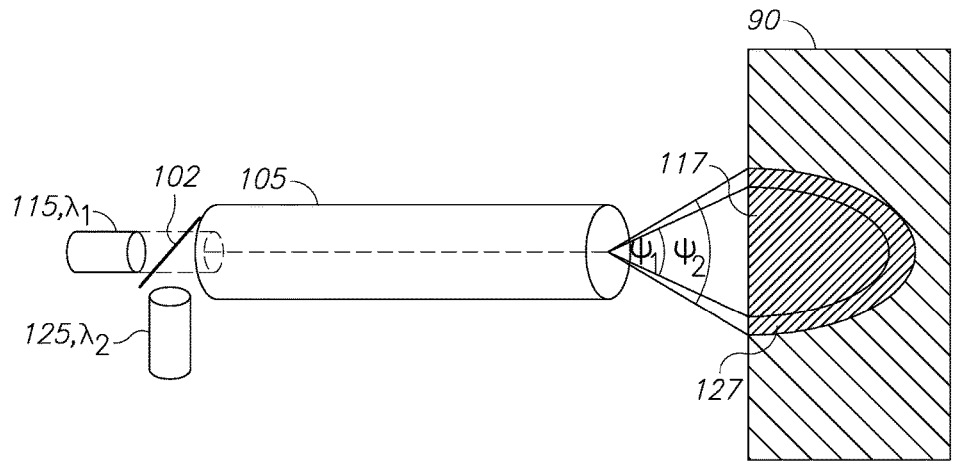
Figure 4D:
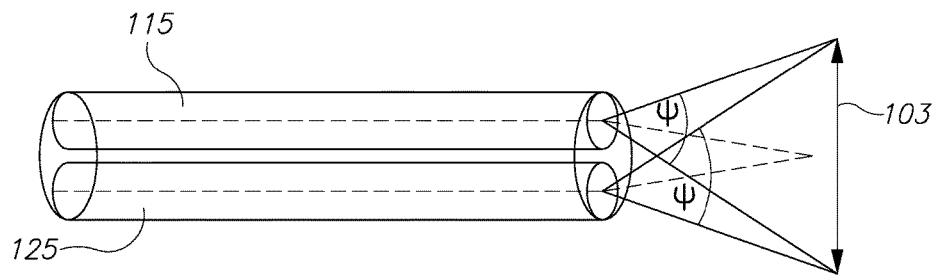
Figure 4E:
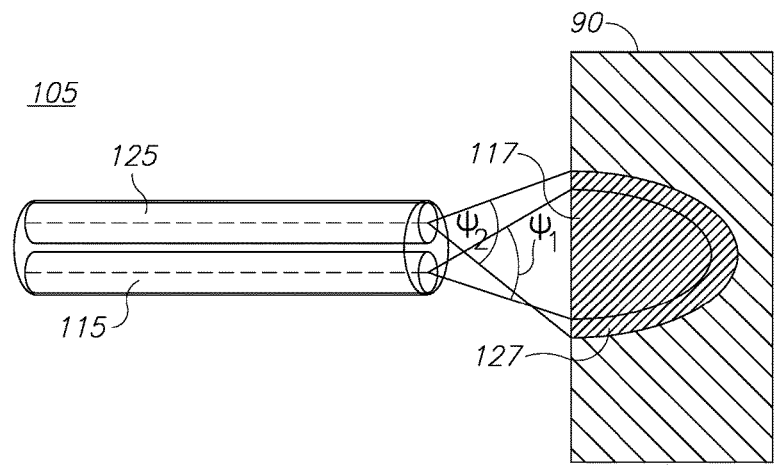

In certain embodiments, the ablative laser as treatment element 115 and the non-ablative laser as stimulation element 125 are delivered through different fiber cores, or through separate fibers or waveguides which are arranged to have the same numerical aperture ψ and/or same field of view (see angles ψ) and/or same beam spread 103. An optical element (not shown) may be associated with any or both signals 116, 126. In certain embodiments, stimulation volume 127 overlaps and encloses treatment volume 117 and comprises additional appropriate safety margin, illustrated in FIG. 4C. FIGS. 4D and 4E schematically illustrate embodiments with separate treatment and stimulation elements 115, 125 (respectively), which may be implemented as single fiber device 105. Treatment and stimulation elements 115, 125 may have similar or varying numerical apertures and beam spreads 103. In certain embodiments any of the parameters numerical apertures ψ, diameters d, wavelength ranges λ, aperture diameter d may vary between treatment and stimulation elements 115, 125 to determine treatment and stimulation volumes 117, 127 under given circumstances or treatments.

FIGS. 5A-5E are high level schematic illustrations of configurations of treatment fiber 105, with treatment element 115 and stimulation element 125, optional electric stimulation element 155 and sensing electrode 135, according to some embodiments of the invention. Any type of electrode arrangement (e.g., dipolar configuration, unipolar configuration, etc.) may be used for sensing electrode 135 and/or electric stimulation element 155. In the present figures, sensing electrode 135 and optional electric stimulation element 155 comprise, in a non-limiting example, two electrodes 135A, 135B and 155A, 155B, respectively.

In certain embodiments, sensing electrode 135A may be attached to or integrated in single fiber 105. In certain embodiments, sensing electrode 135A may be attached downstream of the relevant nerves 80. For example, FIG. 5A schematically illustrates sensing electrode 135A attached to fiber 105 (or to treatment element 115), having optical stimulation element 125 which is also attached to fiber 105. In certain embodiments, optional electrical stimulation electrode 155A may be attached to fiber 105 (or to treatment element 115) similarly to the connection of sensing electrode 135A. A second sensing and/or electric stimulation electrode 135B and/or 155B (respectively) may be attached to fiber 105 at a certain distance from electrode 135A and/or 155B (respectively).

In another example, FIG. 5B schematically illustrates sensing electrode 135A positioned in tissue region 90 (e.g., on the penis in case of a prostate related procedure, see FIG. 1A, at the back region or on a leg in an exemplary microsurgery in at the back region, see FIG. 1B), fiber 105 having optical stimulation element 125 as the same fiber as treatment element 115 or as a separate fiber attached thereto. In certain embodiments, fiber 105 may deliver both treatment and stimulation optical signals (116, 126 and treatment and stimulation elements 125 respectively) and electric stimulation electrode 155A may deliver an electrical stimulation signal 156 (with respect to second electric stimulation electrode 155B).

FIG. 5C schematically illustrates sensing electrode 135B and/or optional electric stimulation electrode 155B as concentric elements with treatment and/or optical stimulation elements 115, 125 respectively, for example within a common jacket 104. Optionally, additional electrical stimulation may be delivered via a concentric electrode 155 with fiber 105 delivering optical stimulation (as stimulation element 125) in addition to the treatment delivered by separate treatment element 115. Sensing electrode 135 may be attached separately to tissue region 90. Clearly, both stimulation element 125 and sensing electrode 135 may be implemented within jacket 104 or attached thereto, either or both concentrically with treatment element 115.

FIG. 5D schematically illustrates sensing electrode(s) 135 and/or optional electric stimulation electrode(s) 155 as enclosing treatment element 115 and/or optical stimulation element 125. In such configurations, probe 105 may be used to combine electric stimulation, optical stimulation and actual treatment. Electrode 135 and/or 155 may be configured as a single electrode (B) with or without a second electrode (A) at a tissue target, or electrode 135 and/or 155 may be implemented to comprise two (or more) electrodes (A and B) within the single tip, implementing e.g. a bipolar configuration. An advantage of a configuration having a rounded tip is that it ensures continuous contact with the tissue during the stimulation while enabling smooth tool movement.

FIG. 5E schematically illustrates probe 105 having a remote electric sensing element 135. Remote electric sensor 135 may be positioned at the tip of probe 105 and be operated by sensor electronic 139 connected via electric wire 138 to a power source and sensing unit 130. In certain embodiments, remote sensor 135 may be arranged to sense magnetic fields. In certain embodiments, non-contact sensor 135 may be arranged to sense any of a radiofrequency (RF) signal, an electric field and a magnetic field.

In certain embodiments, treatment element 115 and optical stimulation element 125 may be implemented as one or more optical fibers that are applied laparoscopically (manually and/or robotically). Treatment element 115 and stimulation element 125 may be implemented as different fiber cores, or as separate waveguides or fibers, and may have a common field of view or cover volumes such that stimulation volume 127 encloses treatment volume 117 (see, e.g., FIG. 3B). Sensing element 135 may, in some embodiments, be implemented remotely, i.e. as respective antennas which are not in direct contact with the location from which sensing measurements are taken and/or the location which is electrically excited (respectively).

In certain embodiments, electric stimulation element 155 may apply electrical stimulation, not necessarily simultaneously with treatment element 115 and/or optical stimulation element 125. Electrical nerve stimulation may be used to coarsely localize the neural structures while the optical nerve stimulation may be used for high resolution nerve localization. In certain embodiments, sensing element 135 may be adapted to perform two types of sensing—one relating to electrical excitation, and another relating to optical excitation of nerves. In certain embodiments, sensing unit 130 may be arranged to map nerves in the treatment area as well as preventing nerve damage during treatment application at a more local level. Control unit 140 may implement decision making algorithms to control the treatment activation (e.g., ablation and/or cutting) according to the received nerve signals (136). In both types of stimulation, sensing results may be used to test function of the nerve structures to early detect intraoperative injury, allowing for immediate corrective measures. Either or both stimulation elements may be implemented in association with treatment element 115 or separated therefrom, relating though to stimulation volume 127 that encloses treatment volume 117.

In certain embodiments, treatment system 100 may comprise treatment unit 110 comprising optical fiber 115 arranged to apply a cold laser ablative treatment to tissue 90 (or target 95 in tissue 90); optical stimulation unit 120 arranged to optically stimulate nerves 80 in tissue 90, in close proximity to location 95 of treatment application; electrical stimulation unit 150 arranged to electrically stimulate nerves 80; sensing unit 130 comprising at least one sensing electrode 135 arranged to sense an electrical signal produced by nerves 80 in tissue 90 in response to the optical stimulation, and to sense an electrical signal produced by nerves 80 in tissue 90 in response to the electrical stimulation; and control unit 140 arranged to control the optical stimulation and the electrical stimulation and control the application of the ablative treatment in realtime and in a closed loop according to the sensed electrical signal produced by nerves in the tissue in response to the optical stimulation. Control unit 140 may be arranged to immediately prevent treatment application upon sensing, by sensing unit 130, of the electrical signal produced by nerves in the tissue in response to the optical stimulation, and to modulate treatment application upon sensing, by sensing unit 130, of the electrical signal produced by nerves in the tissue in response to the electrical stimulation.

Figure 6:
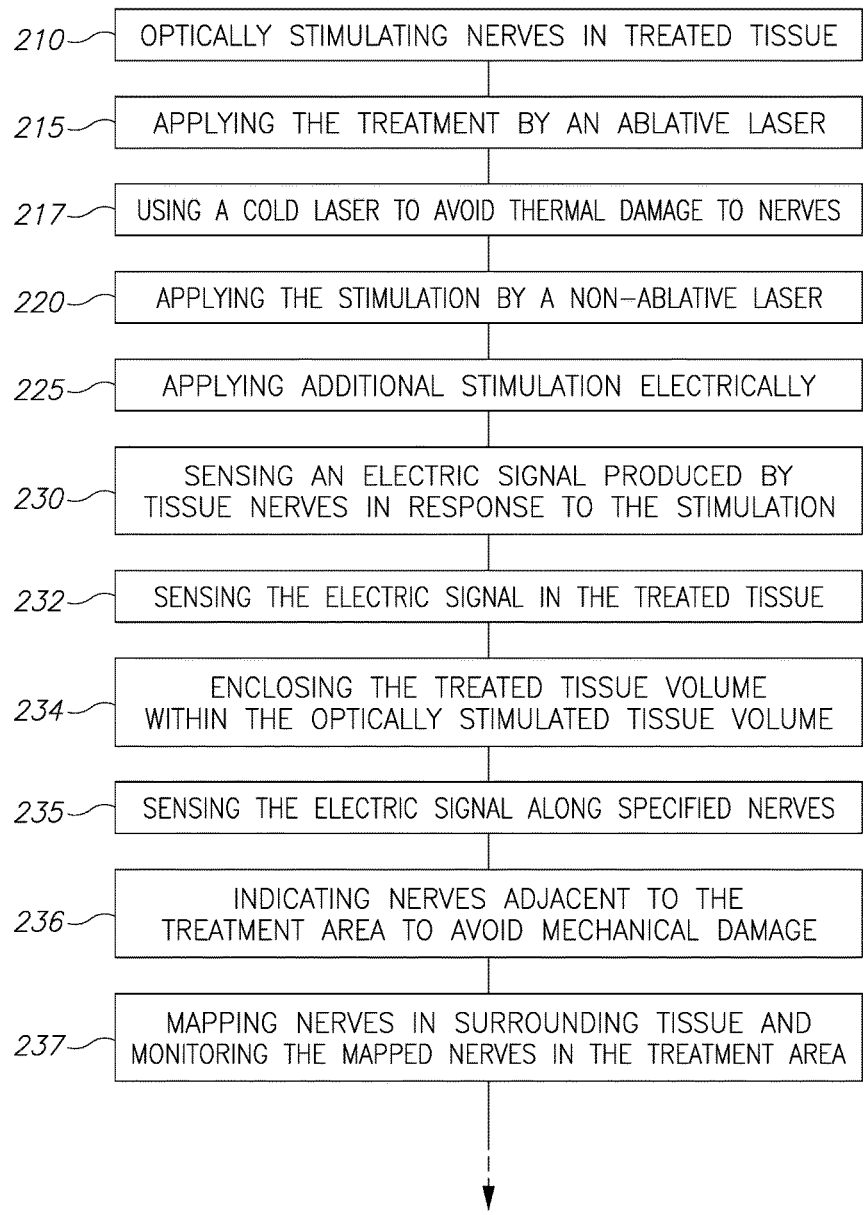
FIG. 6 is a high level schematic flowchart illustrating a method according to some embodiments of the invention.

FIG. 6 is a high level schematic flowchart illustrating a method 200 according to some embodiments of the invention. Method 200 may comprise configuring a tissue treatment system (stage 250) to stimulate nerves in the tissue (stage 210), sense an electrical signal produced by nerves in the tissue (stage 230) in response to the stimulation and control the treatment according to the sensed electrical signal (stage 240). In certain embodiments, the treatment may be carried out by an ablative laser (stage 215) and the stimulation may be carried out by a non-ablative laser (stage 220). A wavelength range of the non-ablative laser may be selected to penetrate the tissue to a larger depth and width than the wavelength range of the ablative laser. In certain embodiments, the stimulation is carried out optically (stage 227) and optionally additional stimulation may be carried out electrically (stage 225).

In certain embodiments, the sensing may be carried out in the treated tissue (stage 232), for example within a specified sensing volume. The treated tissue volume may be enclosed within the stimulated tissue volume (stage 234). In certain embodiments, the sensing may be carried out with respect to specified nerves (stage 235), determined functionally, morphologically or electrically. Furthermore, method 200 may comprise mapping nerves in surrounding tissue and monitoring the mapped nerves in the treatment area (stage 237).

In certain embodiments, method 200 may comprise carrying out nerve preserving surgery procedures, such as nerve preserving tumor removal (stage 260) and nerve-preserving prostatectomy (stage 270).

In certain embodiments, method 200 may comprise configuring a tissue treatment system to optically stimulate nerves in the tissue, sense an electrical signal produced by nerves in the tissue in response to said optical stimulation and control the treatment according to the sensed electrical signal. Method 200 may further comprise immediately preventing treatment application upon sensing the electrical signal produced by nerves in the tissue in response to the optical stimulation. For example, method 200 may comprise interspersing the optical nerve stimulation among pulses of treatment application and immediately preventing a consequent pulse of treatment application upon detection of nerve response to the optical stimulation. The treatment may be optical and method 200 may further comprise configuring the optical stimulation and the optical treatment to differ in at least one of: their respective wavelength or wavelength ranges, their respective incident spot sizes, their respective tissue penetration coefficient and their respective numerical apertures. In certain embodiments, method 200 may comprise electrically stimulating nerves and sensing an electrical signal produced by nerves in the tissue in response to the electrical stimulation. The treated tissue volume may be arranged to be enclosed within a stimulated tissue volume, and the optically stimulated tissue volume may be arranged to be enclosed within an electrically stimulated tissue volume. Method 200 may further comprise providing an alert upon the sensing of the electrical signal in response to the electrical stimulation and/or reconfiguring treatment parameters upon the sensing of the electrical signal in response to the electrical stimulation.

Advantageously, while current technologies enable crude sensing of nerves, at a millimeter scale and prior to the actual treatment or in an open loop and low sensing rate (e.g., using stimulation and sensing electrodes which are mounted and removed prior to the treatment, or are left on the patient and the treatment interrupted at periods to carry out a measurement, or involving the surgery team members in the loop using visual or auditory signals), the current invention allows sensing of nerves on a scale smaller than 1 mm, in realtime during the treatment, and enable implementation of automatic, closed-loop control of the treatment energy emission to avoid damage to nerves. The invention is applicable to any treatment tool, particularly to laser treatment tools.

For example, the current invention may be applied to nerve-preserving tumor removal treatment and be configured to allow maximal tumor removal without damaging nerves adjacent to the tumor.

Advantageously, with respect to known intraoperative neurophysiological monitoring (IONM) techniques which comprise electrical stimulation during operation for nerve monitoring, optical stimulation has a significantly better signal to noise ratio than the electrical stimulation, which enables faster processing time leading to efficient real time implementation. Optical stimulation is also much more localized than electric stimulation, enabling finer and more exact nerve detection, enabling to have the stimulation volume and the treatment volume at the same order of magnitude, leading to high resolution and real time controlled treatment. Combining long range coarse electric stimulation with short range fine optical stimulation enables to avoid both coarse damages (e.g., mechanical damages) and fine damages (e.g., accidental ablation or cutting). Further use of cold laser as the treatment elements provides an additional degree of safety by avoiding thermal damage to nerves.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A treatment probe comprising:
a single probe including:
   a surgical treatment tool having a distal end located at a tip of the probe, and configured to treat a tissue, including to cut, ablate or coagulate the tissue;
   a non-ablative infrared laser comprising an optical fiber configured to send an optical stimulation beam from the tip of the probe to stimulate nerves in the tissue;
   at least one non-contact electric field or magnetic field sensing antenna positioned at a distance of 5 cm or more proximally to the tip of the probe, surrounding the probe and configured to remotely sense an electrical signal produced by the nerves in the tissue without direct contact with the tissue, in response to the optical stimulation beam; and
   a control unit configured to:
   control the non-ablative laser to apply the optical stimulation beam;
   sense, in real time, by the at least one non-contact electric field or magnetic field sensing antenna, if the electrical signal was produced by the nerves in the tissue; and
   control, in real-time, the treatment tool to treat the tissue if no signal was sensed by the non-contact electric field or magnetic field sensing antenna; and
   prevent, in real-time, the treatment tool from treating the tissue if a signal was sensed by the non-contact electric field or magnetic field sensing antenna.

2. The treatment probe of claim 1, wherein the cutting tool comprises one selected from the group consisting of: an ablative laser cutting tool comprising an optical fiber, a radiofrequency electromagnetic radiation (RF) cutting device and microwave radiation cutting device.

3. The treatment probe of claim 1, wherein the control unit is further configured to immediately prevent treatment application upon sensing, by the non-contact electric sensing antenna, the signal produced by the nerves.

4. The treatment probe of claim 1, wherein the control unit is further configured to:
apply a plurality of treatment cycles at a frequency of at least 1 Hz, wherein each treatment cycle from the plurality of treatment cycles comprises:
applying the optical stimulation signal;
sensing if an electrical signal was produced by the nerves in the tissue; and
applying the treatment to the tissue if no signal was sensed.

5. The treatment probe of claim 4, wherein the frequency is at least 10 Hz.

6. The treatment probe of claim 4, wherein the frequency is at least 400 Hz.

7. The treatment probe of claim 1, wherein the single probe further accommodates an electric stimulation electrode, configured to send an electric stimulation signal to the tissue from the tip of the probe, and wherein an additional electric sensing electrode is further configured to sense an electrical signal produced by the nerves in the tissue in response to the electrical stimulation signal.

* * * * *